(12) United States Patent
Lin et al.

(10) Patent No.: US 12,590,329 B2
(45) **Date of Patent: \*Mar. 31, 2026**

(54) REPLICASE CYCLING REACTION (RCR)

(71) Applicants:Shi-Lung Lin, Arcadia, CA (US); Sam Lin, Arcadia, CA (US); Chun-Hung Lin, Taipei (TW)

(72) Inventors: Shi-Lung Lin, Arcadia, CA (US); Sam Lin, Arcadia, CA (US); Chun-Hung Lin, Taipei (TW)

( \* ) Notice: Subject to any disclaimer, the term of this patent is extended or adjusted under 35 U.S.C. 154(b) by 1109 days.

This patent is subject to a terminal disclaimer.

(21) Appl. No.: 17/648,336

(22) Filed: Jan. 19, 2022

(65) Prior Publication Data

US 2022/0411848 A1 Dec. 29, 2022

Related U.S. Application Data

(63) Continuation-in-part of application No. 17/489,357, filed on Sep. 29, 2021.

(60) Provisional application No. 63/280,226, filed on Nov. 17, 2021, provisional application No. 63/270,034, filed on Oct. 20, 2021, provisional application No. 63/222,398, filed on Jul. 15, 2021, provisional application No. 63/212,657, filed on Jun. 19, 2021, provisional application No. 63/210,988, filed on Jun. 15, 2021, provisional application No. 63/209,969, filed on Jun. 12, 2021.

(51) Int. Cl.
*C12Q 1/686* (2018.01)
*C12N 9/12* (2006.01)

(52) U.S. Cl.
CPC .............. *C12Q 1/686* (2013.01); *C12N 9/127* (2013.01); *C12Y 207/07048* (2013.01)

(58) Field of Classification Search
CPC ........ C12Q 2525/161; C12Q 2525/143; C12Q 2521/119
See application file for complete search history.

(56) References Cited

U.S. PATENT DOCUMENTS

| | | | |
|---|---|---|---|
| 6,168,943 | B1 | 1/2001 | Rose |
| 7,662,791 | B2 | 2/2010 | Lin et al. |
| 8,080,652 | B2 | 12/2011 | Lin et al. |
| 8,372,969 | B2 | 2/2013 | Ying et al. |
| 8,609,831 | B2 | 12/2013 | Lin et al. |
| 2019/0330591 | A1 | 10/2019 | Yu et al. |
| 2023/0099592 | A1* | 3/2023 | Lin ...................... C12Q 1/6853 435/6.12 |
| 2023/0242958 | A1* | 8/2023 | Lin ........................ C12P 19/34 435/91.2 |

FOREIGN PATENT DOCUMENTS

WO 2002/092774 A2 11/2002

OTHER PUBLICATIONS

Lin, et al., cDNA library construction using in vitro transcriptional amplification, Methods Mol Biol., 2003;221:93-101.
Bloom, et al., Self-amplifying RNA vaccines for infectious diseases, Gene Therapy, Oct. 22, 2020:117-119.
McDowell, et al., Determination of intrinsic transcription termination efficiency by RNA polymerase elongation fate, Science, Nov. 4, 1994;266(5186):822-825.
Aasen, et al., Isolation and cultivation of human keratinocytes from skin or plucked hair for the generation of induced pluripotent stem cells, Nature protocols, Feb. 2010;5(2):371-382.
Lin, et al., Mir-302 reprograms human skin cancer cells into a pluripotent ES-cell-like state, RNA, Oct. 1, 2008;14 (10):2115-2124.
Lin, et al., Regulation of somatic cell reprogramming through inducible mir-302 expression, Nucleic acids research, Feb. 1, 2011;39(3):1054-1065.
Takahashi, et al., Induction of pluripotent stem cells from mouse embryonic and adult fibroblast cultures by defined factors, Cell, Aug. 25, 2006;126(4):663-676.
Ahn et al., "Biochemical characterization of a recombinant SARS coronavirus nsp12 RNA-dependent RNA polymerase capable of copying viral RNA templates. Archives of Virology." Jul. 13, 2012, vol. 157, pp. 2095-2104.
Chan et al., "Improved Molecular Diagnosis of COVID-19 by the Novel, Highly Sensitive and Specific COVID-19-RdRp/Hel Real-Time Reverse Transcription-PCR Assay Validated In Vitro and with Clinical Specimens.", Journal of Clinical Microbiology. Published online Apr. 23, 2020, vol. 58, No. 5, article No. e00310-20, pp. 1-10.
International Search Report mailed Jun. 16, 2022 for PCT Patent Application No. PCT/US2022/013350.
Ahn et al., Biochemical characterization of a recombinant SARS coronavirus nsp12 RNA-dependent RNA polymerase capable of copying viral RNA templates. Arch Virol. Nov. 2012;157(11):2095-104. doi: 10.1007/s00705-012-1404-x. Epub Jul. 13, 2012.

* cited by examiner

*Primary Examiner* — Young J Kim
(74) *Attorney, Agent, or Firm* — ArentFox Schiff LLP

(57) ABSTRACT

This invention generally relates to a novel RNA/mRNA production and amplification method using viral RNA replicase and/or RNA-dependent RNA polymerase (RdRp) enzymes as well as the associated mRNAs thereof. The present invention can be used for manufacturing and amplifying all varieties of RNA/mRNA sequences carrying at least an RdRp-binding site in the 5'- or 3'-end, or both. The RNA/mRNA so obtained is useful for not only producing mRNA vaccines and/or RNA-based medicines but also for generating the mRNA-associated proteins, peptides, and/or antibodies under an in-vitro as well as in-cell translation condition. Principally, the present invention is a novel RNA replicase-mediated RNA/mRNA amplification method, namely Replicase Cycling Reaction (RCR). The RNA replicases involved in RCR include but not limited to viral and/or bacteriophage RNA-dependent RNA polymerases (RdRp), particularly coronaviral and hepatitis C viral (HCV) RdRp enzymes.

18 Claims, 6 Drawing Sheets
Specification includes a Sequence Listing.

NGN⬛[R]⬛ desired RNA sequence(s) ⬛[Я]⬛A/U-rich

RdRp-binding
site(s)

RdRp-binding
site(s)

RdRp protein only

RCR-ready cDNA/RNA only

RCR-ready cDNA/RNA
+ RdRp protein

← RCR-ready cDNA
templates

RCR-ready RNA
← templates and
RCR-amplified RNAs
(*i.e.* COVID S2 mRNA)

REPLICASE CYCLING REACTION (RCR)

CROSS-REFERENCE TO RELATED APPLICATIONS

The present invention claims priority to U.S. Provisional Patent Application No. 63/209,969 filed on Jun. 12, 2021, which is entitled "Novel mRNA Composition and Production for Use in Anti-Viral and Anti-Cancer Vaccines". The present invention also claims priority to U.S. Provisional Patent Applications No. 63/210,988 filed on Jun. 15, 2021, No. 63/212,657 filed on Jun. 19, 2021, and No. 63/222,398 filed on Jul. 15, 2021, all of which are entitled "Novel mRNA Composition and Production Method for Use in Anti-Viral and Anti-Cancer Vaccines". The present invention further claims priority to U.S. Provisional Patent Applications No. 63/270,034 filed on Oct. 20, 2021, and No. 63/280,226 filed on Nov. 17, 2021, both of which are entitled "Novel RNA Composition and Production Method for Use in iPS Cell Generation". The present application is a continuation-in-part application of the U.S. patent application Ser. No. 17/489,357 filed on Sep. 29, 2021, which is entitled "Novel mRNA Composition and Production Method for Use in Anti-Viral and Anti-Cancer Vaccines". The contents of each application are hereby incorporated by reference in their entirety.

FIELD OF INVENTION

This invention generally relates to a novel RNA/mRNA production and amplification method using viral RNA replicase and/or RNA-dependent RNA polymerase (RdRp) enzymes as well as the associated mRNAs thereof. The present invention can be used for manufacturing and amplifying all varieties of RNA/mRNA sequences carrying at least an RdRp-binding site in the 5'- or 3'-end, or both. The RNA/mRNA so obtained is useful for not only producing mRNA vaccines and/or RNA-based medicines but also for generating the mRNA-associated proteins, peptides, and/or antibodies under an in-vitro as well as in-cell translation condition. Principally, the present invention is a novel RNA replicase-mediated RNA/mRNA amplification method, namely Replicase Cycling Reaction (RCR). The RNA replicases involved in RCR include but not limited to viral and/or bacteriophage RNA-dependent RNA polymerases (RdRp), particularly coronaviral and hepatitis C viral (HCV) RdRp enzymes.

BACKGROUND

Prior polymerase chain reaction (PCR) is a method using thermostable DNA polymerases to amplify double-stranded DNA sequences from DNA templates, no involvement of any RNA material. Unlike PCR, RNA replicase-mediated cycling reaction (RCR) uses RNA-dependent RNA polymerases (RdRp) to amplify single-stranded RNA sequences from RNA templates, no involvement of any DNA material. Clearly, PCR and RCR are very different and definitely not comparable. Hence, previous PCR studies are not related to RCR.

Lin et al. first reported RCR in year 2002 (WO2002/092774 to Lin). Lin had found that using a special design of 5'-cap-capture-molecule-linked primers can trigger some viral and/or bacteriophage repliase-mediated RNA amplification from single-stranded RNA templates. This RCR mechanism mimics some viral or bacteriophage replication/amplification mechanisms. However, the requirement of specific 5'-cap-capture-molecule-linked primers limits its use because many RNA species do not carry 5'-cap molecules. Also, the linked 5'-cap-capture molecules contaminate the resulting RNA products. For mRNA vaccine production, this is problematic because removal of the 5'-cap-capture molecules from the RNA products is tedious and may cause RNA degradation. Hence, a new RCR method without using any 5'-cap-capture-molecule-linked primer is highly desirable.

In this year 2021, another RCR methodolgy was proposed by Bloom et al. (*Gene Therapy* 28:117~129, 2021), using Alphavirus RdRp and its associated binding/recognition site, a 19-nucleotide (nt) 3'-conserved sequence element (3'-CSE). Although Bloom's method does not use any 5'-cap-capture primer, the used 3'-CSE is too long and too structural to be efficiently incorporated into desired RNA templates. In routine practice, to generate RdRp-amplifiable RNA templates, a conventional methodology of polymerase chain reaction-in vitro transcription (PCR-IVT) is commonly used (FIG. 1; U.S. Pat. Nos. 7,662,791, 8,080,652, 8,372,969, and 8,609,831 to Lin; Lin et al., Methods Mol Biol. 221:93~101, 2003). Yet, the 19-nt 3'-CSE is too long and too structural to be placed into PCR primers. Also, because the 3'-CSE is a highly structured RNA sequence, it hinders RNA transcription (McDowell et al., *Science* 266:822~825, 1994) and thus can not be efficiently produced by traditional IVT methods. Moreover, most problematically, the 3'-CSE is specifically recognized by Alphavirus RdRp, which is however not commercially available and hence further hinders the development of its related technology. Given that the properties of different viral replicase/RdRp species are different, it is desirable to search and use another kind of replicase/RdRp enzymes with a more concise and less structural binding/recognition stie for overcoming the problems of prior RCR methods.

In view of the drawbacks of previous RCR methods, it is herein highly desirable to develop a novel RCR methodology not only using a more concise and less structural binding/recognition stie of replicase and/or RdRp but also without using any 5'-cap-capture primer for high efficient RNA amplification and production.

SUMMARY OF THE INVENTION

The principle of the present invention is relied on the incorporation of at least a coronaviral and/or hepatitis C viral (HCV) replicase/RdRp-binding (recognition) site into the 5'- or 3'-ends, or both, of desired RNA templates, leading to the cycling amplification of either the sense strands or antisense strands, or both, of the desired RNA sequences. In RCR, the defined replicase/RdRp-binding sites serve as a promoter and/or enhancer for replicase/RdRp activities. As shown in FIG. 2, after incorporation of at least a replicase/RdRp-binding site into the 5'- and/or 3'-ends of a desired RNA template, the desired RNA sequences can be amplified from about 15 to over 1000 folds in each cycle of replicase/RdRp cycling reaction (RCR). In RCR, the sense-strand RNA sequences are served as templates for amplifying the antisense-strands of the sense-strand RNAs, while the antisense-strand RNA sequences are in turns served as templates for amplifying the sense-strand RNAs. Since each cycle of RCR can provide an about 15 to over 1000 fold RNA amplification rate in a defined time period, depending on the length and structural complexity of the desired RNA sequences, the desired strand(s) of RNA can be obtained in a relatively high purity ratio (maximally 14/15 to >999/1000 purity), depending on the stop point of RCR for the sense-strand or antisense-strand RNAs, or both. Notably, the desired RNA sequences and templates in RCR can be more than one kind and the resulting RNA products can be in either single- or double-stranded conformation.

To prepare RCR-ready RNA templates, we first use reverse transcription-polymerase chain reaction (RT-PCR) to incorporate at least a coronaviral and/or HCV replicase/RdRp-binding site into the 5'- or 3'-ends, or both, of the complementary DNAs (cDNA) of desired RNA sequences. In our special design, at least a replicase/RdRp-binding site is synthetically embedded in each of the PCR primers (called RCR-ready PCR primers) and hence the cDNAs of RCR-ready RNA templates are formed after RT-PCR with the designed replicase/RdRp-binding sites incorporated in the 5'- or 3'-ends, or both. Alternatively, the resulting cDNAs can be cloned into a plasmid or viral vector for further IVT reaction and/or storage preservation. Then, an IVT reaction is performed to generate desired RCR-ready RNA templates from the cDNAs. After that, the resulting RCR-ready RNA templates can be used in RCR to repeatedly amplify and produce the desired RNA sequences. Alternatively, in real practice, since the IVT and RCR can also be performed simultaneously under exactly the same buffer condition, the replicase/RdRp-binding site-incorporated cDNAs (called RCR-ready cDNA templates) are herein also preferred to be served as a starting material for amplifying the desired RNA sequences in a combined IVT-RCR reaction.

After computer screening through over 17 strains of coronaviral and HCV RNA genomes, the present inventors identified several conserved RdRp-binding sites, including 5'- and 3'-end RdRp-binding sites, respectively. In details, the 5'-end RdRp binding site contains at least a sequence of either 5'-AU(G/C)(U/-)G(A/U)~3' (i.e. 5'-AUSUGW~3'; SEQ.ID.NO.1) or 5'-U(C/-) (U/A)C(U/C)(U/A)A~3' (i.e. 5'-UCWCYWA~3'; SEQ.ID.NO.2), or both. Preferably, the 5'-end RdRp binding site is selected from a sequence containing 5'-AUCUGU~3' (SEQ.ID.NO.3), 5'-UCUCUAA~3' (SEQ.ID.NO.4), 5'-UCUCCUA~3' (SEQ.ID.NO. 5), and/or 5'-UUCAA~3' (SEQ.ID.NO.6), or a combination thereof. On the other hand, the 3'-end RdRp binding site contains at least a sequence of either 5'-(U/A)C(A/-)(C/G)AU~3' (i.e. 5'-WCASAU~3'; SEQ.ID.NO. 7) or 5'-U(A/U)(A/G)G(A/U)(G/-)A~3' (i.e. 5'-UWRGWR~3'; SEQ.ID.NO.8), or both. Preferably, the 3'-end RdRp binding site is selected from a sequence containing 5'-ACAGAU~3' (SEQ.ID.NO.9), 5'-UUAGAGA~3' (SEQ.ID.NO.10), 5'-UAGGAGA~3' (SEQ.ID.NO.11), and/or 5'-UUGAA~3' (SEQ.ID.NO.12), or a combination thereof. Also, for facilitating RCR-ready PCR primer designs, the uridine/uracil (U) contents of these RdRp-binding sites can be replaced by thymidine (dT) and/or deoxyuridine (dU) in the primers.

Moreover, for enhancing RNA stability, the uridine/uracil (U) contents of these RdRp-binding sites can be further replaced by pseudouridine or other modified nucleotide analogs during IVT and/or RCR. Due to our novel findings and designs of these RdRp-binding sites, the currently available coronaviral RdRp enzymes can thus be used to efficiently transcribe and amplify either the sense or antisense strands, or both, of desired RNA sequences in vitro, ex vivo as well as in vivo.

Moreover, these newly identified 5'- and 3'-end RdRp-binding sites provide different RNA amplification rates. For example, the amplification rate of SEQ.ID.NO.1 and SEQ.ID.NO.7 is estimated to be ranged from about 25 to 1400 folds per RCR cycle, while that of SEQ.ID.NO.2 and SEQ.ID.NO.8 is ranged from about 10 to 900 folds per RCR cycle, depending on the length and structural complexity of the desired RNA sequences. Due to these different amplification preferences, we can design and use different combinations of these RdRp-binding sites to selectively amplify one RNA strand over the other strand or one kind of RNA strands over the other kind of RNA strands. By this means, a relatively pure single-stranded and/or double-stranded RNA products of the desired RNA sequence(s) can be generated and collected in RCR and then further purified by other methodologies.

In one preferred embodiment, the desired RNA sequence (i.e, mRNA and/or microRNA, or any other kind of RNA species) contains at least an RdRp-binding site in both of its 5'- and 3'-end regions. Since both ends of the desired RNA carry at least an RdRp-binding site for RNA amplification with replicase/RdRp activities, the sense-strand RNA sequences can be used to amplify its complementary antisense RNAs (cRNA or aRNA), while the antisense-strand RNA sequences can be used to amplify the sense RNAs as well, so as to form an amplification cycle of both of the sense- and antisense-strand RNAs and thus resulting in a maximal amplification rate of the desired RNAs. The desired RNAs so obtained can be in either single-stranded or double-stranded conformation, depending on the stop point of RCR. Also, the resulting sense- and antisense-strand RNAs may further form double-stranded RNAs, facilitating the generation of siRNAs, shRNAs, miRNAs, and/or piR-NAs of the desired RNA sequences.

Alternatively, in another preferred embodiment, the desired RNA sequence contains at least an RdRp-binding site in its either 5'-end or 3'-end region. In this way, we can selectively amplify either the sense- or antisense-strand of the desired RNA, leading to more specific amplification of the desired RNA strand. Particularly, this approach is useful for generating and amplifying either the mRNA or the antisense RNA (aRNA) of a specific functional protein, viral antigen or antibody, facilitating the development of mRNA vaccines and/or RNA/antibody-based medicines. The mRNA vaccines and RNA/antibody-based medicines so obtained may help to treat a variety of human diseases, including but not limited to Alzheimer's disease, Parkinson's disease, motor neuron disease, stroke, diabetes, myocardial infraction, hemophilia, anemia, leukemia, and many kinds of cancers as well as many kinds of viral and bacterial infections.

Conceivably, our new RCR methodology can be used to produce and amplify all varieties of RNA species carrying at least an RdRp binding site, particularly viral antigen mRNAs and/or known functional RNAs/mRNAs, which are useful for developing anti-viral and/or anti-disease vaccines as well as medicines, and likely many more. For example, by co-transfection of RCR-ready RNA templates and an isolated coronaviral RdRp mRNA into human somatic cells, our two US priority patent applications (U.S. Provisional Patent Applications No. 63/270,034 and No. 63/280,226 to Lin) had demonstrated a novel method for iPS cell generation. To this, an ordinary skill person in the art can anticipate the use of three-/four-Yamanaka-factor mRNAs (i.e. Oct4/3, Sox2, Nanog and/or Lin~28) to replace the claimed miR~302 precursor microRNA (pre-miRNA) for iPS cell generation as well. Alternatively, as shown in our another priority patent application (U.S. patent application Ser. No. 17/489,357 to Lin), we had developed a new design of RdRp-mediated self-amplifiable RNAs (saRNA) for generating novel mRNA vaccines as well as medicines for treating viral infections and cancers, respectively. Moreover, the RCR-amplified mRNAs can be further used in an in-vitro translation system for producing the encoded proteins, peptides and/or antibodies of interest. In view of these prior invention-proved achievements, many more developments of potential applications of the present invention are highly expected.

To efficiently produce highly structured RNA templates and RdRp mRNA, our priority patent application (U.S. patent application Ser. No. 17/489,357 to Lin) had developed a novel PCR-IVT methodology for overcoming the low efficiency problem of highly structured RNA generation. Traditionally, it is not reasonable for an ordinary skill person in the art to anticipate the effective generation of highly structured RNAs in vitro because it is well known that the presence of hairpin-like RNA structures greatly hinders RNA transcription. In fact, hairpin-like stem-loop structures are signals of intrinsic transcription termination for prokaryotic RNA polymerases (McDowell et al, *Science* 266:822~825, 1994). To solve this problem, our priority method adopts a novel IVT system with a mixture of RNA polymerase and helicase activities. The additional helicase activity in IVT (and likely in RCR as well) markedly reduces the secondary structures of both DNA/RNA templates and the resulting RNA products for far more efficiently producing highly structured RNAs. Accordingly, an improved buffer system is also used to maintain and enhance the efficiency of mixed RNA polymerase/replicase and helicase activities in IVT (and RCR as well). Interestingly, although several prior studies had reported that helicase may be involved in prokaryotic transcription termination, our studies however demonstrate a totally different functionality of helicase in RNA amplification during IVT.

For facilitating intracellular delivery/transfection in vitro, ex vivo or in vivo, the RCR-ready cDNA/RNA template(s) and RdRp mRNA can be mixed, conjugated, encapsulated and/or formulated with at least a delivery/transfection agent selected from, but not limited to, glycylglycerin-derived chemicals, liposomes, nanoparticles, liposomal nanoparticles (LNP), conjugating molecules, infusion/transfusion chemicals, gene gun materials, electroporation agents, transposons/retrotransposons, and a combination thereof.

The advantages of using RCR-ready cDNA/RNA templates for RNA/mRNA production and amplification include (1) high RNA yield rate, (2) high RNA purity, (3) easy preparation in that all reaction materials can be made into a biochemical enzyme kit for performing RCR and/or combined IVT-RCR reactions, (4) simple reaction procedure compatible with other RT-PCR and IVT reactions, (5) simple equipment requirement which can be easily accomplished using a PCR machine or a temperature-controlled incubator, and (6) a variety of potential applications. As a result, it is conceivable that the RCR-ready cDNA/RNA templates of the present invention are very useful for producing and amplifying a variety of desired RNA/mRNA sequences, which can then be used in all sorts of pharmaceutical and therapeutic applications, including but not limited to the development of mRNA vaccines and RNA/microRNA-associated medicines as well as protein/peptide/antibody generation.

A. Definitions

To facilitate understanding of the invention, a number of terms are defined below:

Nucleic Acid: a polymer of deoxyribonucleic acid (DNA) or ribonucleic acid (RNA), either single or double stranded.

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Deoxyribonucleoside Triphosphates (dNTPs): the building block molecules for DNA synthesis, including dATP, dGTP, dCTP, and dTTP and sometimes may further containing some modified deoxyribonucleotide analogs.

Ribonucleoside Triphosphates (rNTPs): the building block molecules for RNA synthesis, including ATP, GTP, CTP, and UTP and sometimes may further containing pseudouridine and some other modified ribonucleotide analogs.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Oligonucleotide: a molecule comprised of two or more monomeric units of DNA and/or RNA, preferably more than three, and usually more than ten. An oligonucleotide longer than 13 nucleotide monomers is also called polynucleotiude. The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleic Acid Composition: a nucleic acid composition refers to an oligonucleotide or polynucleotide such as a DNA or RNA sequence, or a mixed DNA/RNA sequence, in either a single-stranded or a double-stranded molecular structure.

Gene: a nucleic acid composition whose oligonucleotide or polynucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives.

Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a gene without any RNA processing or modification.

Precursor messenger RNA (pre-mRNA): primary RNA transcripts of a protein-coding gene, which are produced by eukaryotic type-II RNA polymerase (Pol-II) machineries in eukaryotes through an intracellular mechanism termed transcription. A pre-mRNA sequence contains a 5'-untranslated region (UTR), a 3'-UTR, exons and introns.

Intron: a part or parts of a gene transcript sequence encoding non-protein-reading frames, such as in-frame intron, 5'-UTR and 3'-UTR.

Exon: a part or parts of a gene transcript sequence encoding protein-reading frames (cDNA), such as cDNA for cellular genes, growth factors, insulin, antibodies and their analogs/homologs as well as derivatives.

Messenger RNA (mRNA): assembly of pre-mRNA exons, which is formed after intron removal by intracellular RNA splicing machineries (e.g. spliceosomes) and served as a protein-coding RNA for peptide/protein synthesis. The peptides/proteins encoded by mRNAs include, but not limited, enzymes, growth factors, insulin, antibodies and their ana-logs/homologs as well as derivatives.

Complementary DNA (cDNA): a single-stranded or double-stranded DNA that contains a sequence complemen-tary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "—" symbol or with an "a" or "antisense" in front of the DNA or RNA, e.g., "aDNA" or "aRNA".

Base Pair (bp): a partnership of adenine (A) with thymine (T), or of cytosine (C) with guanine (G) in a double stranded DNA molecule. In RNA, uracil (U) is substituted for thy-mine. Generally the partnership is achieved through hydro-gen bonding. For example, a sense nucleotide sequence "5'-A-T-C-G-U~3" can form complete base pairing with its antisense sequence "5'-A-C-G-A-T~3".

5'-end: a terminus lacking a nucleotide at the 5' position of successive nucleotides in which the 5'-hydroxyl group of one nucleotide is joined to the 3'-hydroyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, RNA or DNA, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA mol-ecule, double-stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Homologous or Homology: a term indicating the similar-ity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides.

Complementary or Complementarity or Complementa-tion: a term used in reference to matched base pairing between two polynucleotides (i.e. sequences of an mRNA and a cDNA) related by the aforementioned "base pair (bp)" rules. For example, the sequence "5'-A-G-T~3" is comple-mentary to not only the sequence "5'-A-C-T~3" but also to "5'-A-C-U~3". Complementation can be between two DNA strands, a DNA and an RNA strand, or between two RNA strands. Complementarity may be "partial" or "complete" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complemen-tation means that half of the bases were mismatched and half were matched. Two strands of nucleic acid can be comple-mentary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (tem-plate), such complexes (or hybrids) are sufficiently stable to serve the priming function required by a DNA polymerase to initiate DNA synthesis. There is a specific, i.e. non-random, interaction between two complementary polynucleotides that can be competitively inhibited.

Posttranscriptional Gene Silencing: a targeted gene knockout or knockdown effect at the level of mRNA deg-radation or translational suppression, which is usually trig-gered by either foreign/viral DNA or RNA transgenes or small inhibitory RNAs.

RNA Interference (RNAi): a posttranscriptional gene silencing mechanism in eukaryotes, which can be triggered by small inhibitory RNA molecules such as microRNA (miRNA), small hairpin RNA (shRNA) and small interfer-ing RNA (siRNA). These small RNA molecules usually function as gene silencers, interfering with expression of intracellular genes containing either completely or partially complementary to the small RNAs.

MicroRNA (miRNA): single-stranded RNAs capable of binding to targeted gene transcripts that have partial comple-mentarity to the miRNA. MiRNA is usually about 17~27 oligonucleotides in length and is able to either directly degrade its intracellular mRNA target(s) or suppress the protein translation of its targeted mRNA, depending on the complementarity between the miRNA and its target mRNA. Natural miRNAs are found in almost all eukaryotes, func-tioning as a defense against viral infections and allowing regulation of gene expression during development of plants and animals.

Precursor MicroRNA (Pre-miRNA): hairpin-like single-stranded RNAs containing stem-arm and stem-loop regions for interacting with intracellular RNaseIII endoribonu-cleases to produce one or multiple microRNAs (miRNAs) capable of silencing a targeted gene or genes complementary to the microRNA sequence(s). The stem-arm of a pre-miRNA can form either a perfectly (100%) or a partially (mis-matched) hybrid duplexes, while the stem-loop con-nects one end of the stem-arm duplex to form a circle or hairpin-loop conformation. In the present invention, how-ever, precursor of microRNA may also includes pri-miRNA.

Small interfering RNA (siRNA): short double-stranded RNAs sized about 18~27 perfectly base-paired ribonucleotide duplexes and capable of degrading target gene transcripts with almost perfect complementarity.

Small or short hairpin RNA (shRNA): single-stranded RNAs that contain a pair of partially or completely matched stem-arm nucleotide sequences divided by an unmatched loop or bubble oligonucleotide to form a hairpin-like structure. Many natural miRNAs are derived from small hairpin-like RNA precursors, namely precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or pol~2) promoter, or both, a Kozak consensus translation initiation site, polyadenylation signals, a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, perhaps binds to, and initiates RNA transcription. For the purposes of the instant invention, a promoter can be a known polymerase binding site, an enhancer and the like, any sequence that can initiate synthesis of RNA transcripts by a desired polymerase.

RNA Processing: a cellular mechanism responsible for RNA maturation, modification and degradation, including RNA splicing, intron excision, exosome digestion, non-sense-mediated decay (NMD), RNA editing, RNA processing, 5'-capping, 3'-poly(A) tailing, and a combination thereof.

Gene Delivery: a genetic engineering method selected from the group consisting of polysomal transfection, liposomal transfection, chemical (nanoparticle) transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Transfected Cell: a single or a plurality of eukaryotic cells after being artificially inserted with at least a nucleic acid sequence or protein/peptide molecule into the cell(s), selected from the group consisting of a somatic cell, a tissue cell, a stem cell, a germ-line cell, a tumor cell, a cancer cell, a virus-infected cell, and a combination thereof.

Antibody: a peptide or protein molecule having a pre-selected conserved domain structure coding for a receptor capable of binding a pre-selected ligand.

Pharmaceutical and/or therapeutic Application: a bio-medical utilization and/or apparatus useful for stem cell generation, drug/vaccine development, non-transgenic gene therapy, cancer therapy, disease treatment, wound healing, tissue/organ repair and regeneration, and high-yield production of proteins/peptides/antibodies, drug ingredients, medicines, vaccines and/or food supplies, and a combination thereof.

B. Compositions and Applications

A novel RNA replicase-mediated RNA amplification method, comprising:

(a) providing at least an RNA sequence, wherein said RNA sequence contains at least a 5'-end or 3'-end RdRp binding site, or both;

(b) providing at least an RNA replicase, wherein said RNA replicase is isolated or modified from the RNA-dependent RNA polymerases (RdRp) of coronavirus or hepatitis C virus (HCV); and (c) mixing the RNA sequence of (a) and the RNA replicase of (b) under a buffer condition, so as to elicit RNA replicase-mediated production and amplification of said RNA sequence, wherein said buffer condition contains ribonucleoside triphosphate molecules (rNTPs) required for RNA synthesis and is in a pH range from 6.0 to 8.0 as well as in a temperature range from 20° C. to 45° C.

For coronaviral and/or HCV RdRp enzymes, the 5'-end RdRp binding site contains at least a sequence of either 5'-AUSUGW~3' (SEQ.ID.NO.1) or 5'-UCWCYWA~3' (SEQ.ID.NO.2), or both. Preferably, the 5'-end RdRp binding site is selected from an RNA sequence containing 5'-AUCUGU~3' (SEQ.ID.NO.3), 5'-UCUCUAA~3' (SEQ.ID.NO.4), 5'-UCUCCUA~3' (SEQ.ID.NO.5), and/or 5'-UUCAA~3' (SEQ.ID.NO.6), or a combination thereof. On the other hand, the 3'-end RdRp binding site contains at least a sequence of either 5'-WCASAU~3' (SEQ.ID.NO.7) or 5'-UWRGWR~3' (SEQ.ID.NO.8), or both. Preferably, the 3'-end RdRp binding site is selected from an RNA sequence containing 5'-ACAGAU~3' (SEQ.ID.NO.9), 5'-UUA-GAGA~3 ' (SEQ.ID.NO.10), 5'-UAGGAGA~3' (SEQ.ID.NO. 11), and/or 5'-UUGAA~3' (SEQ.ID.NO.12), or a combination thereof. For incorporating these RdRp-binding sites into PCR primers, the uridine/uracil (U) contents of these RdRp-binding sites can be replaced by thymidine (dT) and/or deoxyuridine (dU) in the primers. Also, for enhancing RNA stability, the uridine/uracil (U) contents of these RdRp-binding sites as well as the resulting RNA products can be replaced by pseudouridine or other modified nucleotide analogs.

BRIEF DESCRIPTION OF THE DRAWINGS

Referring particularly to the drawings for the purpose of illustration only and not limitation, there is illustrated.

EXAMPLES

1. Human Cell Isolation and Cultivation

Figure 1:
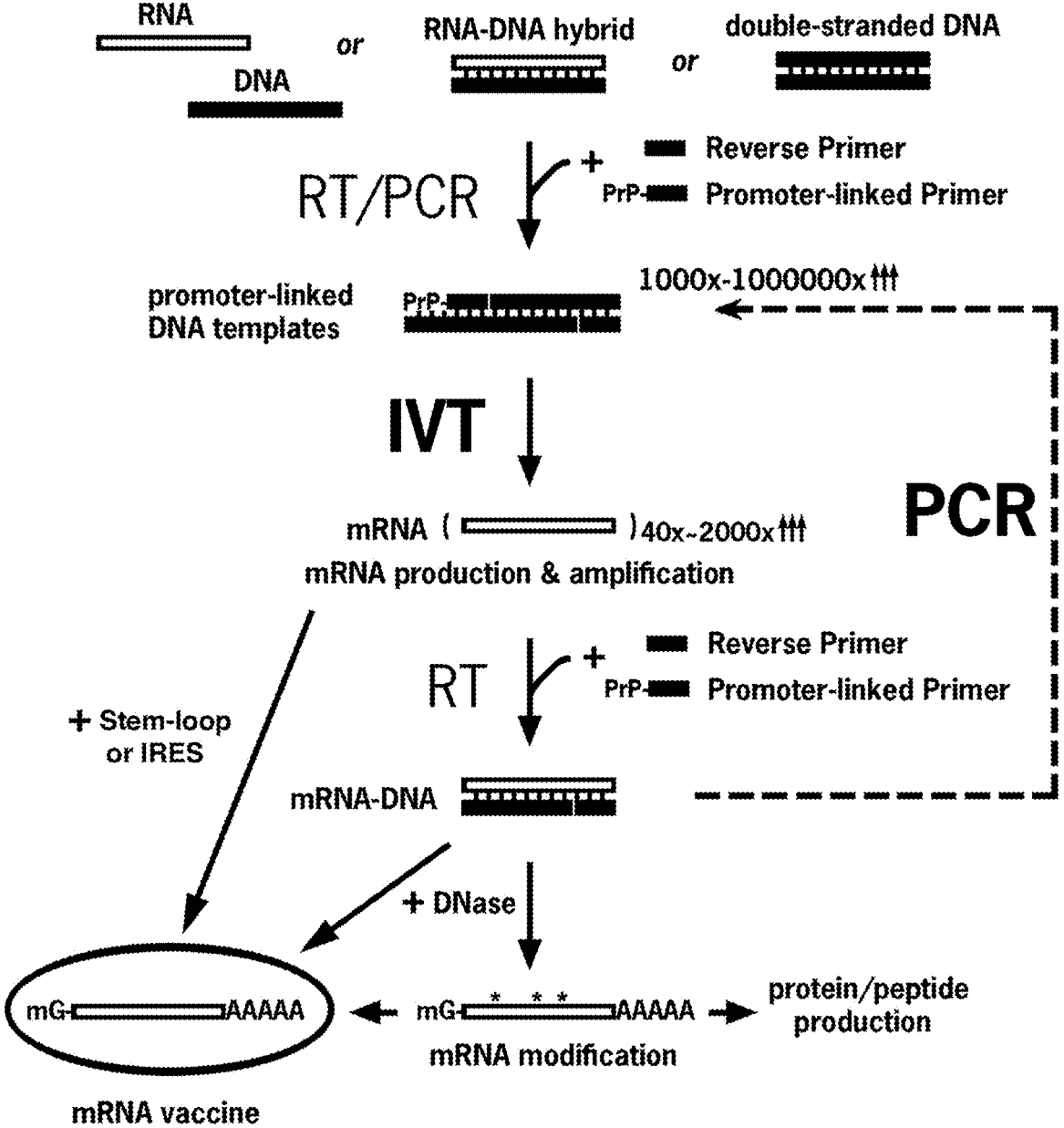
FIG. 1 depicts the step-by-step procedure of the prior PCR-IVT methodology. For RNA production, a part or whole procedure of this PCR-IVT method can be adopted for either single or multiple cycle amplification of desired RNA products.
Figure 2:
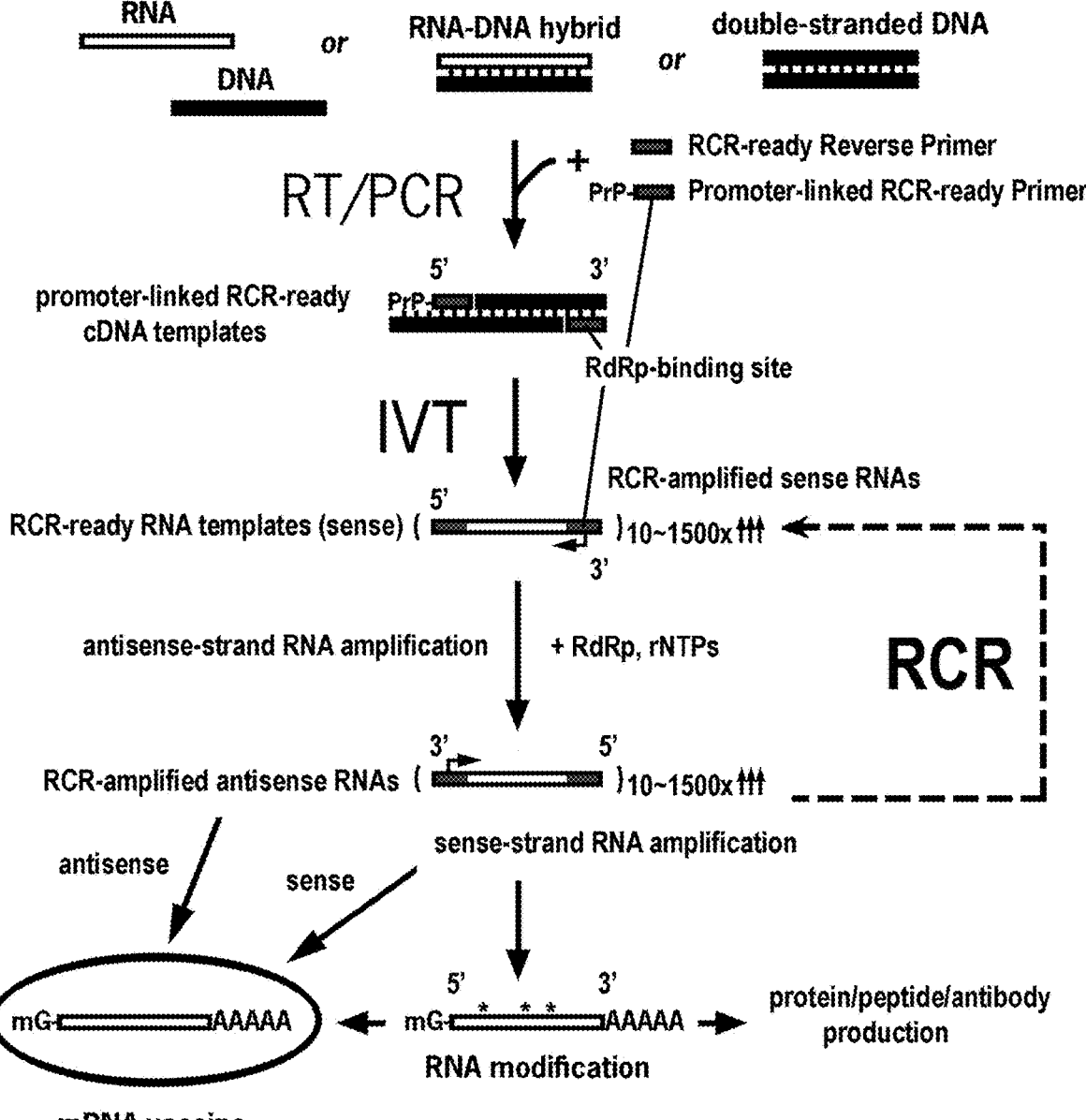
FIG. 2 depicts the step-by-step procedure of the presently invented RCR methodology. For preparing RCR-ready cDNA/RNA templates, at least a coronaviral and/or HCV replicase/RdRp-binding site is incorporated into the 5'- or 3'-ends, or both, of the cDNAs of desired RNA sequences, using conventional RT-PCR methods. Then, a part or whole procedure of this novel RCR method is used to produce and amplify the desired RNA sequences from the RCR-ready cDNA/RNA templates after single or multiple cycle amplification. Alternatively, since IVT and RCR methods can be performed simultaneously under the same buffer condition, the RCR-ready cDNA/RNA templates can also be used as starting materials for amplifying the desired RNA sequences in a combined IVT-RCR reaction.
Figure 3:
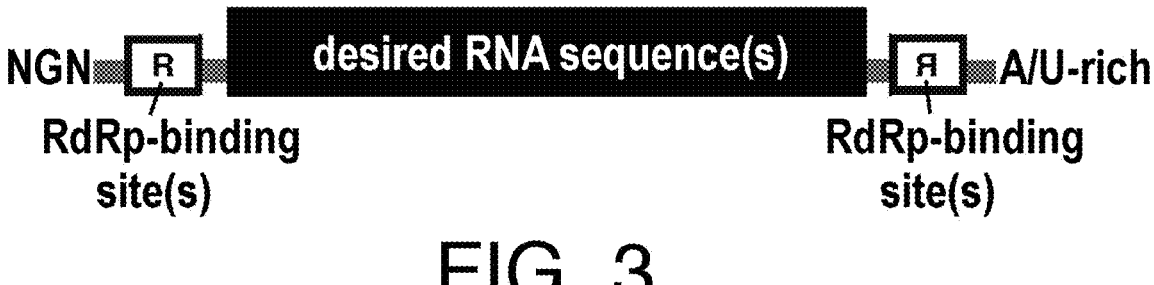
FIG. 3 depicts the designed structures of RCR-ready cDNA/RNA templates. It is noted that the RCR-ready cDNA templates are in double-stranded DNA conformation (useful for IVT and combined IVT-RCR reactions), while the RCR-ready RNA templates are in single-stranded RNA conformation (useful for RCR). For further enhancing the stability of RCR-ready RNA templates, the uridine/uracil (U) contents of the templates can be replaced by pseudouridine or other modified nucleotide analogs.
Figure 4:
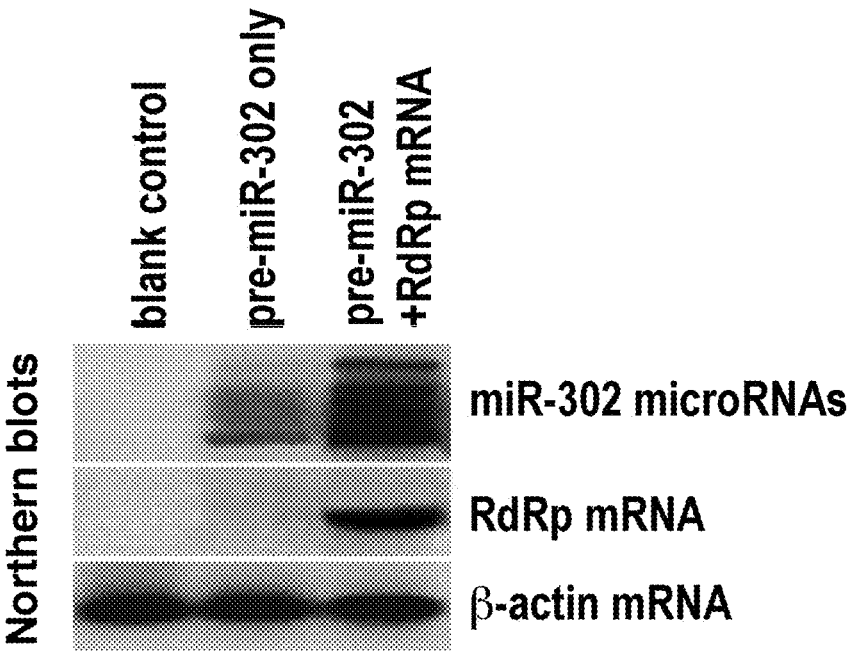
FIG. 4 shows the Northern blot analysis results of markedly increased expressions of miR~302 microRNAs (i.e. from top to bottom: b, c, d, a) and RdRp mRNA in transfected human cells after co-transfection with RCR-ready miR~302 precursor microRNA (pre-miR~302) and viral RdRp mRNA templates (as shown in most right) compared to the result of cells transfected with only the pre-miR~302 template (in middle), demonstrating the evidence of RCR in cells.
Figure 5:
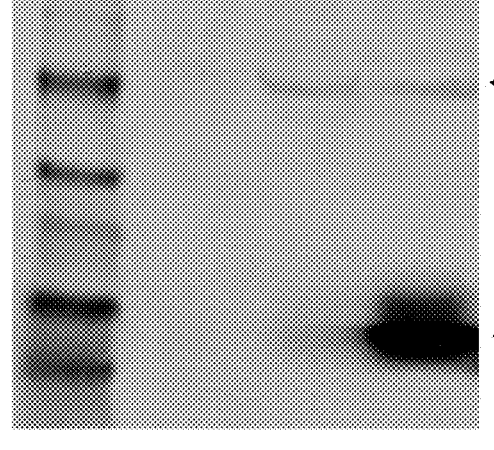
FIG. 5 shows Northern blot analysis results of RCR-ready cDNA and RNA templates as well as the resulting amplified RNA products of interest (i.e. mRNA sequences of viral antigen proteins/peptides), demonstrating the evidence of RCR in vitro.
Figure 6:
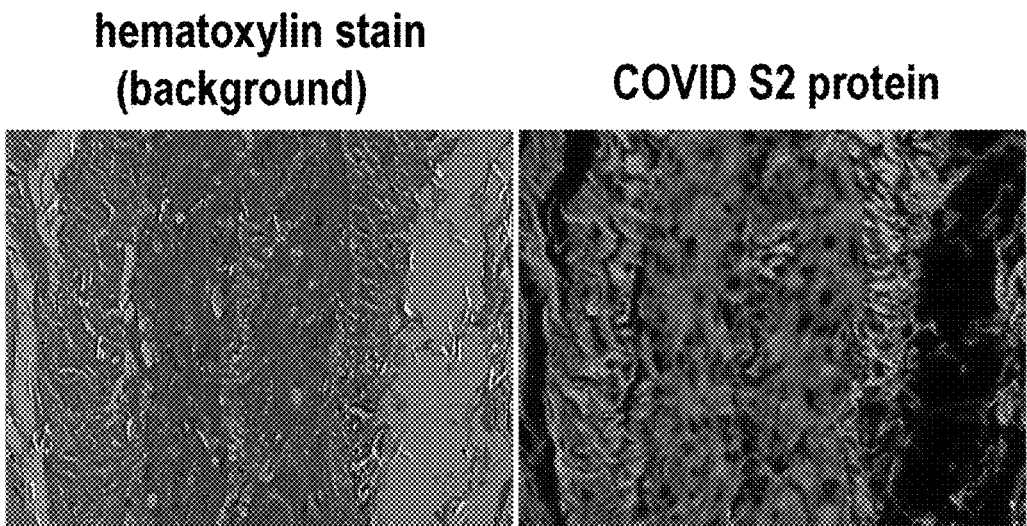
FIG. 6 shows the immunohistochemical staining of coronaviral (e.g. COVID~19) S 2 proteins produced in the mouse muscle cells in vivo after co-transfection with RCR-amplified S protein mRNA (from FIG. 5) and isolated RdRp mRNA (from FIG. 4), indicating that the present invention is useful for developing and manufacturing anti-viral mRNA vaccines.

Starting tissue cells can be obtained from either enzymatically dissociated skin cells using Aasen's protocol (Nat. Protocols 5, 371~382, 2010) or simply from the buffy coat fraction of heparin-treated peripheral blood cells. The isolated tissue samples must be kept fresh and used immediately by mixing with 4 mg/mL collagenase I and 0.25% TrypLE for 15~45 min, depending on cell density, and rinsed by HBSS containing trypsin inhibitor two times and then transferred to a new sterilized microtube containing 0.3 mL of feeder-free SFM culture medium (IrvineScientific, CA). After that, cells were further dissociated by shaking in a microtube incubator for 1 min at 37° C. and then transferred the whole 0.3 mL cell suspension to a 35-mm Matrigel-coated culture dish containing 1 mL of feeder-free SFM culture medium supplemented with formulated pre-miR~302+RdRp mRNA mixture, LIF, and bFGF/FGF2, or other optional defined factors. The concentrations of pre-miR~302+RdRp mRNA mixture, LIF, bFGF/FGF2, and other optional defined factors are ranged from 0.1 to 500 microgram (μg)/mL, respectively, in the cell culture medium. The cell culture medium and all of the supplements must be refreshed every 2~3 days and the cells are passaged at about 50%~60% confluence by exposing the cells to trypsin/EDTA for 1 min and then rinsing two times in HBSS containing trypsin inhibitor. For ASC expansion, the cells were replated at 1:5~1:500 dilution in fresh feeder-free MSC Expansion SFM culture medium supplemented with formulated pre-miR~302+RdRp mRNA mixture, LIF, bFGF/FGF2, and/or other optional defined factors. For culturing keratinocytes, cells are isolated from skin tissues and cultivated in EpiLife serum-free cell culture medium supplemented with human keratinocyte growth supplements (HKGS, Invitrogen, Carlsbad, CA) in the presence of proper antibiotics at 37° C. under 5% $CO_2$. Culture cells are passaged at 50%~60% confluency by exposing cells to trypsin/EDTA solution for 1 min and rinsing once with phenol red-free DMEM medium (Invitrogen), and the detached cells are replated at 1:10 dilution in fresh EpiLife medium with HKGS supplements. Human cancer and normal cell lines A549, MCF7, PC3, HepG2, Colo~829 and BEAS~2B were obtained either from the American Type Culture Collection (ATCC, Rockville, MD) or our collaborators and then maintained according to manufacturer's or provider's suggestions. After reprogramming, the resulting iPS cells (iPSCs) were cultivated and maintained following either Lin's feeder-free or Takahashi's feeder-based iPSC culture protocols (Lin et al., RNA 14:2115~2124, 2008; Lin et al., *Nucleic Acids Res.* 39:1054~1065, 201~1; Takahashi K and Yamanaka S, Cell 126:663~676, 2006).

2. In-Vitro RNA Transfection

For intracellular delivery/transfection, 0.5~200 μg of RCR-amplified RNA/mRNA (i.e. pre-miR~302 or coronaviral S protein mRNA) and RdRp mRNA mixture (ratio ranged from about 20:1 to 1:20) is dissolved in 0.5 ml of fresh cell culture medium and mixed with 1~50 μl of In-VivoJetPEI or other similar transfection reagents. After 10~30 min incubation, the mixture is then added into a cell culture containing 50%~60% confluency of the cultivated cells. The medium is reflashed every 12 to 48 hours, depending on cell types. This transfection procedure may be performed repeatedly to increase transfection efficiency.

3. Preparation of RCR-Ready cDNA/RNA Templates

Reverse transcription (RT) of desired RNA/mRNA is performed by adding about 0.01 ng~10 microgram (m) of isolated RNA/mRNA into a 20~50 μL RT reaction (SuperScript III cDNA RT kit, ThermoFisher Scientific, MA, USA), following the manufacturer's suggestions. Depending on the RNA/mRNA amount, the RT reaction mixture further contains about 0.01~20 nmole RT primer, a proper amount of deoxyribonucleoside triphosphate molecules (dNTPs) and reverse transcriptase in 1×RT buffer. Then, the RT reaction is incubated at 37~65° C. for 1~3 hours (hr), depending on the length and structural complexity of the desired RNA/mRNA sequences, so as to make the complementary DNA (cDNA) templates thereof for the next step of PCR. For isolation of viral RdRp mRNA, we had designed and used an RT-reverse primer 5'-GACAACAGGT GCGCTCAGGT CCT~3' (SEQ.ID.NO.13) to generate coronaviral RdRp cDNA.

Next, polymerase chain reaction (PCR) is performed by adding about 0.01 pg~10 μg of the RT-derived cDNAs into a 20~50 μL PCR preparation mixture (High-Fidelity PCR master kit, ThermoFisher Scientific, MA, USA), following the manufacturer's suggestions. Then, the PCR mixture is first incubated in five to twenty (5~20) cycles of denaturation at 94° C. for 1 mim, annealing at 30~55° C. for 30 sec~1 min, and then extension at 72° C. for 1~3 min, depending on the structure and length of the desired cDNA sequences. After that, another ten to twenty (10~20) cycles of PCR are performed with a series of sequential cycling steps of denaturation at 94° C. for 1 mim, annealing at 50~58° C. for 30 sec, and then extension at 72° C. for 1~3 min, depending on the structure and length of the resulting PCR products. Finally, the resulting PCR products are used as cDNA templates for IVT and RCR. For IVT-RCR template preparation, we design and use a specific pair of RCR-ready PCR primers for incorporating the identified RdRp-binding sites into the PCR-derived RdRp cDNA templates, including SEQ.ID.NO.13 and 5'-GATATCTAAT ACGACTCACT ATAGGGAGAG GTATGGTACT TGGTAGTT~3' (SEQ.ID.NO.14). Later, a 5'-cap molecule may be further incorporated in the resulting mRNA products of IVT-RCR. On the other hand, we also design and use another pair of RCR-ready PCR primers for incorporating the identified RdRp-binding sites into the PCR-derived cDNA templates of human pre-miR~302 familial cluster (pre-miR~302), including 5'-GATATCTAAT ACGACT-CACT ATAGGGAGAT CTGTGGGAAC TAGTTCAGGA AGGTAA~3' (SEQ.ID.NO.15) and 5'-GTTCTCCTAA GCCTGTAGCC AAGAACTGCA CA~3' (SEQ.ID.NO.16). In the primer design, various sequences and combinations of RNA promoters and RdRp-binding sites can be used, such as T7, T3 and/or SP6 promoter, and at least an RdRp binding site has been incorporated in the 5'- and/or 3'-end primers.

For generating RCR-ready RNA/mRNA templates, since at least a promoter and at least an RdRp-binding site have been incorporated into the resulting PCR-derived cDNA products (served as RCR-ready cDNA templates), an IVT-RCR reaction can then be performed to amplify desired RNA/mRNA sequences from the cDNA templates. The IVT-RCR reaction mixture contains 0.01 ng~10 μg of the PCR-derived cDNA product, 0.1~50 U of isolated corona-viral RdRp/helicase (Abeam, MA, USA/Creative Enzymes, NY), a proper amount of ribonucleoside triphosphate molecules (rNTPs) and RNA polymerase (i.e. T7, T3, or SP6) in 1× transcription buffer. The transcription buffer is commercially available and may be further adjusted according to the manufacturer's suggestions. Preferably, the 1× transcription buffer may further contain 0.001~10 mM of betaine (trimethylglycine, TMG), dimethylsulfoxide (DMSO), and/or 3-(N-morpholino)propane sulfonic acid (MOPS), and/or a combination thereof. Then, the IVT-RCR reaction is incubated at 30~40° C. for 1~6 hr, depending on the stability and activity of the used RdRp and RNA polymerase enzymes.

4. Novel RCR Protocol

The starting RCR mixture contains about 0.01 ng~10 μg of the RCR-ready RNA/mRNA templates, about 0.1~50 U of isolated coronaviral RdRp/helicase, and a proper amount of rNTPs in 1× transcription buffer. RdRp/helicase is either an RdRp enzyme with an additional RNA unwinding activity or a mixture of RdRp and helicase. The transcription buffer is commercially available in the market and may be further adjusted according to the manufacturer's suggestions. Additionally, the 1× transcription buffer may further contain 0.001~10 mM of betaine (trimethylglycine, TMG), dimethylsulfoxide (DMSO), and/or 3-(N-morpholino)pro-pane sulfonic acid (MOPS), and/or a combination thereof, which facilitates the denaturation of highly structured RNA/DNA sequences, such as hairpins and stem-loop structures. After that, the RCR reaction is incubated at 20~45° C. for 1~6 hr, depending on the stability and activity of the used RdRp enzymes.

5. RNA Purification and Northern Blot Analysis

Desired RNAs (10 μg) are isolated with a mirVana> RNA isolation kit (Ambion, Austin, TX) or similar purification filter column, following the manufacturer's protocol, and then further purified by using either 5%~10% TBE-urea polyacrylamide or 1%~3.5% low melting point agarose gel electrophoresis. For Northern blot analysis, the gel-fractionated RNAs are electroblotted onto a nylon membrane. Detection of the RNA and its IVT template (the PCR-derived cDNA product) is performed with a labeled [LNA]-DNA probe complementary to a target sequence of the desired RNA. The probe is further purified by high-performance liquid chromatography (HPLC) and tail-labeled with terminal transferase (20 units) for 20 min in the presence of either a dye-labeled nucleotide analog or [$^{32}$P]-dATP (>3000 Ci/mM, Amersham International, Arlington Heights, IL).

6. Protein Extraction and Western Blot Analysis

Cells ($10^6$) are lysed with a CelLytic-M lysis/extraction reagent (Sigma) supplemented with protease inhibitors, Leupeptin, TLCK, TAME and PMSF, following the manufacturer's suggestion. Lysates are centrifuged at 12,000 rpm for 20 min at 4° C. and the supernatant is recovered. Protein concentrations are measured using an improved SOFTmax protein assay package on an E-max microplate reader (Molecular Devices, CA). Each 30 μg of cell lysate are added to SDS-PAGE sample buffer under reducing (+50 mM DTT) and non-reducing (no DTT) conditions, and boiled for 3 min before loading onto a 6~8% polyacylamide gel. Proteins are resolved by SDS-polyacrylamide gel electrophoresis (PAGE), electroblotted onto a nitrocellulose membrane and incubated in Odyssey blocking reagent (Li-Cor Biosciences, Lincoln, NB) for 2 hr at room temperature. Then, a primary antibody is applied to the reagent and incubated the mixture at 4° C. After overnight incubation, the membrane is rinsed three times with TBS-T and then exposed to goat anti-mouse IgG conjugated secondary antibody to Alexa Fluor 680 reactive dye (1:2,000; Invitrogen-Molecular Probes), for 1 hr at the room temperature. After three additional TBS-T rinses, fluorescent scanning of the immunoblot and image analysis are conducted using Li-Cor Odyssey Infrared Imager and Odyssey Software v.10 (Li-Cor).

7. Immunostaining Assay

Cell/Tissue samples are fixed in 100% methanol for 30 min at 4° C. and then 4% paraformaldehyde (in 1×PBS, pH 7.4) for 10 min at 20° C. After that, the samples are incubated in 1×PBS containing 0.1%~0.25% Triton X~100 for 10 min and then washed in 1×PBS three times for 5 min. For immunostaining, primary antibodies were purchased from Invitrogen (CA, USA) and Sigma-Aldrich (MO, USA), respectively. Dye-labeled goat anti-rabbit or horse anti-mouse antibody are used as the secondary antibody (Invitrogen, CA, USA). Results are examined and analyzed at 100× or 200× magnification under a fluorescent 80i microscopic quantitation system with a Metamorph imaging program (Nikon).

8. In Vivo Transfection Assay

The mixture of RCR-amplified RNA/mRNA and RdRp mRNA (ratio ranged from about 20:1 to 1:20) is mixed well with a proper amount of delivery agent, such as an In-VivoJetPEl transfection reagent or other similar LNP-based delivery/transfection agents, following the manufacturer's protocol, and then injected into blood veins or muscles of an animal, depending the purpose of applications. The delivery/transfection agent is used for mixing, conjugating, encapsulating or formulating the amplified RNA/mRNA and RdRp mRNA mixture, so as to not only protect the RNA contents from degradation but also facilitate the delivery/transfection of the RNA/mRNA and RdRp mRNA mixture into specific target cells of interest in vitro, ex vivo and/or in vivo.

15 | 16

9. Statistic Analysis

All data were shown as averages and standard deviations (SD). Mean of each test group was calculated by AVERAGE of Microsoft Excel. SD was performed by STDEV. Statistical analysis of data was performed by One-Way ANOVA. Tukey and Dunnett's t post hoc test were used to identify the significance of data difference in each group. $p < 0.05$ was considered significant (SPSS v12.0, Claritas Inc).

REFERENCES

1. WO2002/092774 to Shi-Lung Lin et al.
2. U.S. Pat. No. 7,662,791 to Shi-Lung Lin et al.
3. U.S. Pat. No. 8,080,652 to Shi-Lung Lin et al.
4. U.S. Pat. No. 8,372,969 to Ying SY and Shi-Lung Lin.
5. U.S. Pat. No. 8,609,831 to Shi-Lung Lin and Ying SY.
6. Shi-Lung Lin and Ji H; cDNA library construction using in-vitro transcriptional amplification. *Methods Mol Biol.* 221:93~101, 2003.
7. Bloom et al; Self-amplifying RNA vaccines for infectious diseases. *Gene Therapy* 28:117~129, 2021.
8. McDowell et al.; Determination of intrinsic transcription termination efficiency by RNA polymerase elongation rate. *Science* 266:822~825, 1994.
9. Aasen et al.; Isolation and cultivation of human keratinocytes from skin or plucked hair for the generation of induced pluripotent stem cells. *Nat. Protocols* 5:371~382, 2010.
10. Shi-Lung Lin et al.; Mir-302 reprograms human skin cancer cells into a pluripotent ES-cell-like state. *RNA* 14:2115-2124, 2008.
11. Shi-Lung Lin et al.; Regulation of somatic cell reprogramming through inducible mir-302 expression. *Nucleic Acids Res.* 39:1054-1065, 2011.
12. Takahashi K and Yamanaka S; Induction of pluripotent stem cells from mouse embryonic and adult fibroblast cultures by defined factors. *Cell* 126:663-676, 2006.

```
SEQUENCE LISTING
(1) GENERAL INFORMATION:
(iii) NUMBER OF SEQUENCES: 16

(2) INFORMATION FOR SEQ ID NO: 1:
(i) SEQUENCE CHARACTERISTICS:
(A) LENGTH: 6 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 1:
AUSUGW                                                    6

(2) INFORMATION FOR SEQ ID NO: 2:
(i) SEQUENCE CHARACTERISTICS:
(A) LENGTH: 7 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 2:
UCWCYWA                                                   7

(2) INFORMATION FOR SEQ ID NO: 3:
(i) SEQUENCE CHARACTERISTICS:
(A) LENGTH: 6 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 3:
AUCUGU                                                    6

(2) INFORMATION FOR SEQ ID NO: 4:
(i) SEQUENCE CHARACTERISTICS:
```

-continued

```
(A) LENGTH: 7 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 4:
UCUCUAA                                                                7

(2) INFORMATION FOR SEQ ID NO: 5:
(i) SEQUENCE CHARACTERISTICS:
(A) LENGTH: 7 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 5:
UCUCCUA                                                                7

(2) INFORMATION FOR SEQ ID NO: 6:
(i) SEQUENCE CHARACTERISTICS:
(A) LENGTH: 5 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 6:
UUCAA                                                                  5

(2) INFORMATION FOR SEQ ID NO: 7:
(i) SEQUENCE CHARACTERISTICS:
(A) LENGTH: 6 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 7:
WCASAU                                                                 6

(2) INFORMATION FOR SEQ ID NO: 8:
(i) SEQUENCE CHARACTERISTICS:
(A) LENGTH: 6 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 8:
```

```
-continued
UWRGWR                                                              6

(2) INFORMATION FOR SEQ ID NO: 9:
(i) SEQUENCE CHARACTERISTICS:
(A) LENGTH: 6 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 9:
ACAGAU                                                             6

(2) INFORMATION FOR SEQ ID NO: 10:
(i) SEQUENCE CHARACTERISTICS:
(A) LENGTH: 7 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 10:
UUAGAGA                                                            7

(2) INFORMATION FOR SEQ ID NO: 11:
(i) SEQUENCE CHARACTERISTICS:
(A) LENGTH: 7 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 11:
UAGGAGA                                                            7

(2) INFORMATION FOR SEQ ID NO: 12:
(i) SEQUENCE CHARACTERISTICS:
(A) LENGTH: 5 base pairs
(B) TYPE: nucleic acid
(C) STRANDEDNESS: single
(D) TOPOLOGY: linear (ii) MOLECULE TYPE: RNA
(A) DESCRIPTION: /desc = "synthetic"

(iii) HYPOTHETICAL: NO (iv) ANTI-SENSE: NO (xi) SEQUENCE DESCRIPTION: SEQ ID NO: 12:
UUGAA                                                              5

(2) INFORMATION FOR SEQ ID NO: 13:
(i) SEQUENCE CHARACTERISTICS:
(A) LENGTH: 23 base pairs
(B) TYPE: nucleic acid
(C) STRANDEDNESS: single
(D) TOPOLOGY: linear (ii) MOLECULE TYPE: DNA
(A) DESCRIPTION: /desc = "synthetic"

(iii) HYPOTHETICAL: NO
```

(iv) ANTI-SENSE: YES (xi) SEQUENCE DESCRIPTION: SEQ ID NO: 13:
GACAACAGGT GCGCTCAGGT CCT                                                   23

(2) INFORMATION FOR SEQ ID NO: 14:
(i) SEQUENCE CHARACTERISTICS:
(A) LENGTH: 48 base pairs
(B) TYPE: nucleic acid
(C) STRANDEDNESS: single
(D) TOPOLOGY: linear (ii) MOLECULE TYPE: DNA
(A) DESCRIPTION: /desc = "synthetic"

(iii) HYPOTHETICAL: NO (iv) ANTI-SENSE: NO (xi) SEQUENCE DESCRIPTION: SEQ ID NO: 14:
GATATCTAAT ACGACTCACT ATAGGGAGAG GTATGGTACT TGGTAGTT                        48

(2) INFORMATION FOR SEQ ID NO: 15:
(i) SEQUENCE CHARACTERISTICS:
(A) LENGTH: 56 base pairs
(B) TYPE: nucleic acid
(C) STRANDEDNESS: single
(D) TOPOLOGY: linear (ii) MOLECULE TYPE: DNA
(A) DESCRIPTION: /desc = "synthetic"

(iii) HYPOTHETICAL: NO (iv) ANTI-SENSE: NO (xi) SEQUENCE DESCRIPTION: SEQ ID NO: 15:
GATATCTAAT ACGACTCACT ATAGGGAGAT CTGTGGGAAC TAGTTCAGGA AGGTAA 56

(2) INFORMATION FOR SEQ ID NO: 16:
(i) SEQUENCE CHARACTERISTICS:
(A) LENGTH: 32 base pairs
(B) TYPE: nucleic acid
(C) STRANDEDNESS: single
(D) TOPOLOGY: linear (ii) MOLECULE TYPE: DNA
(A) DESCRIPTION: /desc = "synthetic"

(iii) HYPOTHETICAL: NO (iv) ANTI-SENSE: YES (xi) SEQUENCE DESCRIPTION: SEQ ID NO: 16:
GTTCTCCTAA GCCTGTAGCC AAGAACTGCA CA                                         32

---

SEQUENCE LISTING

<160> NUMBER OF SEQ ID NOS: 16

<210> SEQ ID NO 1
<211> LENGTH: 6
<212> TYPE: RNA
<213> ORGANISM: Artificial Sequence
<220> FEATURE:
<223> OTHER INFORMATION: Synthetic

<400> SEQUENCE: 1 ausugw                                                                      6

<210> SEQ ID NO 2
<211> LENGTH: 7
<212> TYPE: RNA
<213> ORGANISM: Artificial Sequence

```
<220> FEATURE:
<223> OTHER INFORMATION: Synthetic

<400> SEQUENCE: 2 ucwcywa                                                                           7

<210> SEQ ID NO 3
<211> LENGTH: 6
<212> TYPE: RNA
<213> ORGANISM: Artificial Sequence
<220> FEATURE:
<223> OTHER INFORMATION: Synthetic

<400> SEQUENCE: 3 aucugu                                                                            6

<210> SEQ ID NO 4
<211> LENGTH: 7
<212> TYPE: RNA
<213> ORGANISM: Artificial Sequence
<220> FEATURE:
<223> OTHER INFORMATION: Synthetic

<400> SEQUENCE: 4 ucucuaa                                                                           7

<210> SEQ ID NO 5
<211> LENGTH: 7
<212> TYPE: RNA
<213> ORGANISM: Artificial Sequence
<220> FEATURE:
<223> OTHER INFORMATION: Synthetic

<400> SEQUENCE: 5 ucuccua                                                                           7

<210> SEQ ID NO 6
<211> LENGTH: 5
<212> TYPE: RNA
<213> ORGANISM: Artificial Sequence
<220> FEATURE:
<223> OTHER INFORMATION: Synthetic

<400> SEQUENCE: 6 uucaa                                                                             5

<210> SEQ ID NO 7
<211> LENGTH: 6
<212> TYPE: RNA
<213> ORGANISM: Artificial Sequence
<220> FEATURE:
<223> OTHER INFORMATION: Synthetic

<400> SEQUENCE: 7 wcasau                                                                            6

<210> SEQ ID NO 8
<211> LENGTH: 6
<212> TYPE: RNA
<213> ORGANISM: Artificial Sequence
<220> FEATURE:
<223> OTHER INFORMATION: Synthetic

<400> SEQUENCE: 8 uwrgwr                                                                            6
```

-continued

```
<210> SEQ ID NO 9
<211> LENGTH: 6
<212> TYPE: RNA
<213> ORGANISM: Artificial Sequence
<220> FEATURE:
<223> OTHER INFORMATION: Synthetic

<400> SEQUENCE: 9 acagau                                                              6

<210> SEQ ID NO 10
<211> LENGTH: 7
<212> TYPE: RNA
<213> ORGANISM: Artificial Sequence
<220> FEATURE:
<223> OTHER INFORMATION: Synthetic

<400> SEQUENCE: 10 uuagaga                                                             7

<210> SEQ ID NO 11
<211> LENGTH: 7
<212> TYPE: RNA
<213> ORGANISM: Artificial Sequence
<220> FEATURE:
<223> OTHER INFORMATION: Synthetic

<400> SEQUENCE: 11 uaggaga                                                             7

<210> SEQ ID NO 12
<211> LENGTH: 5
<212> TYPE: RNA
<213> ORGANISM: Artificial Sequence
<220> FEATURE:
<223> OTHER INFORMATION: Synthetic

<400> SEQUENCE: 12 uugaa                                                               5

<210> SEQ ID NO 13
<211> LENGTH: 23
<212> TYPE: DNA
<213> ORGANISM: Artificial Sequence
<220> FEATURE:
<223> OTHER INFORMATION: Synthetic

<400> SEQUENCE: 13
gacaacaggt gcgctcaggt cct                                           23

<210> SEQ ID NO 14
<211> LENGTH: 48
<212> TYPE: DNA
<213> ORGANISM: Artificial Sequence
<220> FEATURE:
<223> OTHER INFORMATION: Synthetic

<400> SEQUENCE: 14
gatatctaat acgactcact atagggagag gtatggtact tggtagtt               48

<210> SEQ ID NO 15
<211> LENGTH: 56
<212> TYPE: DNA
<213> ORGANISM: Artificial Sequence
<220> FEATURE:
<223> OTHER INFORMATION: Synthetic
```

-continued

<400> SEQUENCE: 15
gatatctaat acgactcact atagggagat ctgtgggaac tagttcagga aggtaa          56

<210> SEQ ID NO 16
<211> LENGTH: 32
<212> TYPE: DNA
<213> ORGANISM: Artificial Sequence
<220> FEATURE:
<223> OTHER INFORMATION: Synthetic

<400> SEQUENCE: 16
gttctcctaa gcctgtagcc aagaactgca ca                                    32

---

The invention claimed is:

1. An RNA replicase-mediated RNA amplification method, comprising:
   (a) providing at least a linear RNA sequence, wherein said RNA sequence contains at least a 5'-end RdRp binding site and at least a 3'-end RdRp binding site, wherein said 5'-end RdRp binding site is SEQ ID NO: 2 and said 3'-end RdRp binding site is homologous to any one of SEQ ID NO: 8, 10, or 11;
   (b) providing at least an RNA replicase, wherein said RNA replicase is isolated or modified from the RNA-dependent RNA polymerases (RdRp) of coronavirus; and
   (c) mixing the RNA sequence of (a) and the RNA replicase of (b) under a buffer condition, so as to elicit RNA replicase-mediated production and amplification of said RNA sequence, wherein said buffer condition contains ribonucleoside triphosphate molecules (rN-TPs) required for RNA synthesis and is in a pH range from 6.0 to 8.0 as well as in a temperature range from 20° C. to 45° C., thereby producing amplified RNA sequences.

2. The method as defined in claim 1, wherein said RNA sequence contains at least a sense- or antisense-strand conformation.

3. The method as defined in claim 1, wherein said 5'-end RdRp binding site is SEQ.ID.NO.4.

4. The method as defined in claim 1, wherein said 3'-end RdRp binding site is SEQ.ID.NO. 8.

5. The method as defined in claim 1, wherein the 5'-end and 3'-end RdRp binding sites of said RNA sequence remain incorporated in the amplified RNA sequences of said RNA sequence.

6. The method defined in claim 1, wherein said buffer condition comprises a 1× transcription buffer.

7. The method as defined in claim 1, wherein said ribonucleoside triphosphate molecules (rNTPs) include ATP, GTP, CTP and UTP.

8. The method as defined in claim 1, wherein said ribonucleoside triphosphate molecules (rNTPs) further contain pseudouridine analogs.

9. The method as defined in claim 1, wherein the uridine/uracil (U) contents of said RNA sequence are pseudouridine analogs.

10. The method as defined in claim 1, wherein the amplified RNA sequences are further formulated with at least a delivery agent for facilitating intracellular transfection.

11. The method as defined in claim 10, wherein said delivery agent includes liposomal nanoparticles (LNP).

12. The method as defined in claim 1, wherein said RNA sequence is mRNA.

13. The method as defined in claim 12, wherein said mRNA is a medicine material.

14. The method as defined in claim 12, wherein said mRNA encodes at least an antibody.

15. The method as defined in claim 1, wherein said RNA sequence is precursor microRNA (pre-miRNA).

16. The method as defined in claim 15, wherein said pre-miRNA is an anti-cancer drug.

17. The method as defined in claim 15, wherein said pre-miRNA is an inducer material for generating iPS cells.

18. The method as defined in claim 1, wherein said RNA sequence is a pharmaceutical ingredient in medicines or therapies.

* * * * *